United States Patent
Marci et al.

(10) Patent No.: US 12,369,809 B2
(45) Date of Patent: *Jul. 29, 2025

(54) DETERMINING INTENSITY OF A BIOLOGICAL RESPONSE TO A PRESENTATION

(71) Applicant: The Nielsen Company (US), LLC, New York, NY (US)

(72) Inventors: Carl Marci, Boston, MA (US); Dereck Padden, Somerville, MA (US); Randall Rule, Belmont, MA (US); Joonho Moon, Kingston, MA (US); Brendan Murray, Boston, MA (US)

(73) Assignee: The Nielsen Company (US), LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/561,461

(22) Filed: Dec. 23, 2021

(65) Prior Publication Data
US 2022/0117510 A1      Apr. 21, 2022

Related U.S. Application Data

(63) Continuation of application No. 16/434,998, filed on Jun. 7, 2019, now Pat. No. 11,213,219, which is a
(Continued)

(51) Int. Cl.
*A61B 5/0533* (2021.01)
*A61B 5/00* (2006.01)
(Continued)

(52) U.S. Cl.
CPC .......... *A61B 5/0533* (2013.01); *A61B 5/7271* (2013.01); *G06Q 30/0201* (2013.01);
(Continued)

(58) Field of Classification Search
CPC . A61B 5/0533; A61B 5/7271; A61B 2503/12; G06Q 30/0201; G06Q 30/0242; G16H 40/63
See application file for complete search history.

(56) References Cited

U.S. PATENT DOCUMENTS 2,013,013 A      9/1935  Van Valkenburg
5,676,138 A *   10/1997  Zawilinski ............. A61B 3/113
                                                                600/301
(Continued)

OTHER PUBLICATIONS

Watching Ads is Real Science Research Companies Monitor Physiological Reactions to Commercials to Determine Their Effectiveness.: [3 Star Edition] Bruce Horvitz Los Angeles Times. Orlando Sentinel [Orlando, Fla] Sep. 1, 1991: D1.*
(Continued)

*Primary Examiner* — Timothy Padot

(57) ABSTRACT

Example methods, apparatus, systems, and articles of manufacture for determining intensity of a biological response to a presentation are disclosed. An example apparatus includes at least one memory and processor circuitry to execute instructions to identify trough-to-peak instances in first galvanic skin response (GSR) data for a first subject, the first GSR data collected from the first subject during exposure of the first subject to media content during a period of time; assign trough-to-peak scores to corresponding ones of the trough-to-peak instances; associate the respective ones of the trough-to-peak scores with a time corresponding to the trough of each trough-to-peak instances; assign window scores to corresponding ones of windows in the period of time based on the highest trough-to-peak score occurring within the corresponding windows to generate a first GSR intensity profile; and identify an element of the media content for modification based on the first GSR intensity profile.

20 Claims, 8 Drawing Sheets

Related U.S. Application Data continuation of application No. 15/089,955, filed on Apr. 4, 2016, now Pat. No. 10,314,510.

(60) Provisional application No. 62/272,932, filed on Dec. 30, 2015.

(51) Int. Cl.
  *G06Q 30/0201* (2023.01)
  *G06Q 30/0242* (2023.01)
  *G16H 40/63* (2018.01)

(52) U.S. Cl.
  CPC ......... *G06Q 30/0242* (2013.01); *G16H 40/63* (2018.01); *A61B 2503/12* (2013.01)

(56) References Cited

U.S. PATENT DOCUMENTS

| | | | |
|---|---|---|---|
| 6,190,314 B1 | 2/2001 | Ark et al. | |
| 6,292,688 B1* | 9/2001 | Patton | A61B 5/378 600/545 |
| 6,422,999 B1* | 7/2002 | Hill | A61B 5/395 600/300 |
| 6,453,241 B1* | 9/2002 | Bassett, Jr. | G16B 25/10 435/6.1 |
| 8,684,742 B2 | 4/2014 | Siefert | |
| 8,793,715 B1 | 7/2014 | Weitzenfeld et al. | |
| 10,314,510 B2 | 6/2019 | Marci et al. | |
| 11,213,219 B2 | 1/2022 | Marci et al. | |
| 2002/0194081 A1* | 12/2002 | Perkowski | H04L 51/10 705/26.1 |
| 2003/0093792 A1* | 5/2003 | Labeeb | H04N 21/26283 725/38 |
| 2006/0041548 A1* | 2/2006 | Parsons | G06F 16/954 707/999.005 |
| 2007/0146637 A1* | 6/2007 | Johnson | G06Q 30/02 351/226 |
| 2007/0162927 A1* | 7/2007 | Ramaswamy | H04N 21/235 725/32 |
| 2007/0250901 A1* | 10/2007 | McIntire | H04N 21/47815 348/E7.071 |
| 2008/0091512 A1* | 4/2008 | Marci | G06Q 10/10 705/7.29 |
| 2008/0097854 A1* | 4/2008 | Young | G06Q 30/0242 705/14.43 |
| 2008/0222670 A1 | 9/2008 | Lee et al. | |
| 2009/0088610 A1 | 4/2009 | Lee et al. | |
| 2009/0131764 A1* | 5/2009 | Lee | A61B 5/0205 600/301 |
| 2009/0328089 A1 | 12/2009 | Pradeep et al. | |
| 2010/0004977 A1* | 1/2010 | Marci | H04N 21/44218 705/7.32 |
| 2010/0211439 A1* | 8/2010 | Marci | H04N 21/4662 705/7.29 |
| 2010/0290538 A1 | 11/2010 | Xu et al. | |
| 2011/0142413 A1* | 6/2011 | Kang | G06F 16/437 348/E5.002 |
| 2012/0253921 A1* | 10/2012 | Pradeep | G06Q 30/0251 705/14.42 |
| 2013/0103624 A1* | 4/2013 | Thieberger | G06N 20/00 706/12 |
| 2013/0343614 A1 | 12/2013 | Kyal et al. | |
| 2014/0108309 A1* | 4/2014 | Frank | G06Q 50/01 706/12 |
| 2014/0161421 A1* | 6/2014 | Shoemaker | G11B 27/28 386/278 |
| 2014/0195221 A1* | 7/2014 | Frank | G06N 7/01 704/9 |
| 2014/0378859 A1 | 12/2014 | Taratorin et al. | |
| 2015/0185993 A1* | 7/2015 | Wheatley | H04N 21/4621 715/744 |
| 2015/0264431 A1 | 9/2015 | Cheng | |
| 2017/0188876 A1 | 7/2017 | Marci et al. | |

OTHER PUBLICATIONS

They know what you want: if neuromarketers can find the key to our consumer desires, will they be able to manipulate what we buy. Singer, Emily. New Scientist 183.2458: 36(2). Reed Business Information Ltd. (Jul. 31, 2004).*

D.M. Alexander et al., Separating individual skin conductance responses in a short interstimulus-interval paradigm. Journal of Neuroscience Methods 146 (2005) 116-123.*

W. Z. Khan, Y. Xiang, M. Y. Aalsalem and Q. Arshad, "Mobile Phone Sensing Systems: A Survey," in IEEE Communications Surveys & Tutorials, vol. 15, No. 1, pp. 402-427, First Quarter 2013.*

Emily Singer, "They Know What You Want: If Neuromarketers Can Find the Key to Our Consumer Desires, Will They be Able to Manipulate What We Buy", New Scientist 183.2458: 36(2). Reed Business Information Ltd. (Jul. 31, 2004), 5 pages.

D.M. Alexander et al., "Separating individual skin conductance responses in a short interstimulus-interval paradigm." Journal of Neuroscience Methods, 146 (2005), pp. 116-123, 8 pages.

Rami N. Khushaba et al. "Consumer neuroscience: Assessing the brain response to marketing stimuli using electroencephalogram (EEG) and eye tracking," Expert Systems with Applications, 40 (2013), pp. 3803-3812, 10 pages.

Bruce Horvitz, "Watching Ads is Real Science Research Companies Monitor Physiological Reactions to Commercials to Determine Their Effectiveness," Orlando Sentinel, Sep. 1, 1991, D1, 4 pages.

United States Patent and Trademark Office, "Notice of Allowance and Fee(s) Due," issued in connection with U.S. Appl. No. 16/434,998, dated Aug. 26, 2021, 11 pages.

United States Patent and Trademark Office, "Non-Final Office Action," issued in connection with U.S. Appl. No. 15/089,955 dated Apr. 20, 2018, 22 pages.

United States Patent and Trademark Office, "Final Office Action," issued in connection with U.S. Appl. No. 15/089,955 dated Sep. 6, 2018, 31 pages.

United States Patent and Trademark Office, "Notice of Allowance and Fee(s) Due," issued in connection with U.S. Appl. No. 15/089,955 dated Jan. 28, 2019, 12 pages.

United States Patent and Trademark Office, "Non-Final Office Action," issued in connection with U.S. Appl. No. 16/434,998, dated Jul. 18, 2019, 18 pages.

United States Patent and Trademark Office, "Final Office Action," issued in connection with U.S. Appl. No. 16/434,998, dated Mar. 24, 2020, 17 pages.

United States Patent and Trademark Office, "Advisory Action," issued in connection with U.S. Appl. No. 16/434,998, dated Jun. 5, 2020, 3 pages.

United States Patent and Trademark Office, "Non-Final Office Action," issued in connection with U.S. Appl. No. 16/434,998, dated Jul. 7, 2020, 20 pages.

United States Patent and Trademark Office, "Final Office Action," issued in connection with U.S. Appl. No. 16/434,998, dated Dec. 23, 2020, 21 pages.

United States Patent and Trademark Office, "Advisory Action," issued in connection with U.S. Appl. No. 16/434,998, dated Apr. 6, 2021, 3 pages.

United States Patent and Trademark Office, "Non-Final Office Action," issued in connection with U.S. Appl. No. 16/434,998, dated May 12, 2021, 10 pages.

* cited by examiner

DETERMINING INTENSITY OF A BIOLOGICAL RESPONSE TO A PRESENTATION

RELATED APPLICATIONS

This patent arises from a continuation of U.S. patent application Ser. No. 16/434,998, now U.S. Pat. No. 11,213,219, which was filed Jun. 7, 2019, and titled "DETERMINING INTENSITY OF A BIOLOGICAL RESPONSE TO A PRESENTATION." U.S. patent application Ser. No. 16/434,998 is a continuation of U.S. application Ser. No. 15/089,955, now U.S. Pat. No. 10,314,510, which was filed on Apr. 4, 2016, and titled "DETERMINING INTENSITY OF A BIOLOGICAL RESPONSE TO A PRESENTATION." U.S. patent application Ser. No. 16/434,998 claims the benefit under 35 U.S.C. § 119(e) to U.S. Provisional Patent Application No. 62/272,932, which was filed on Dec. 30, 2015, and titled "DETERMINING INTENSITY OF A BIOLOGICAL RESPONSE TO A PRESENTATION." U.S. patent application Ser. No. 16/434,998, U.S. application Ser. No. 15/089,955, and U.S. Provisional Patent Application No. 62/272,932 are hereby incorporated by reference in their entireties. Priority to U.S. patent application Ser. No. 16/434,998, U.S. application Ser. No. 15/089,955, and U.S. Provisional Patent Application No. 62/272,932 is hereby claimed.

FIELD OF THE DISCLOSURE

This disclosure relates generally to biological responses and, more particularly, to determining intensity of a biological response to a presentation.

BACKGROUND

Galvanic skin response is a type of a biological response indicative of arousal.

Figure 1:
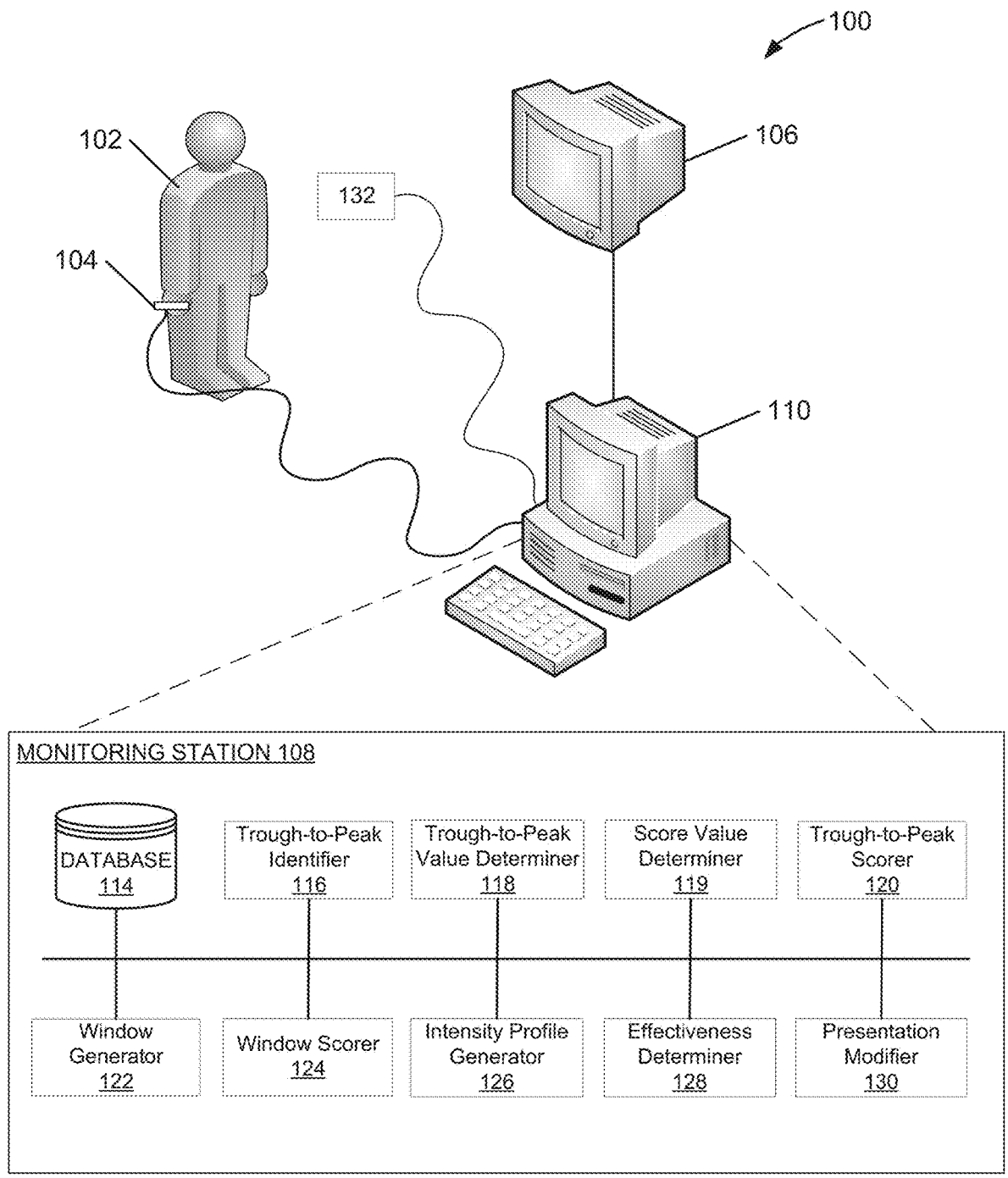
FIG. 1 illustrates an example intensity measurement system including an example monitoring station constructed in accordance with the teachings of this disclosure.

Certain examples are shown in the above-identified figures and described in detail below. In describing these examples, like or identical reference numbers are used to identify the same or similar elements. The figures are not necessarily to scale and certain features and certain views of the figures may be shown exaggerated in scale or in schematic for clarity and/or conciseness. Additionally, several examples have been described throughout this specification. Any features from any example may be included with, a replacement for, or otherwise combined with other features from other examples.

DETAILED DESCRIPTION

Disclosed herein are example methods, apparatus/systems and articles of manufacture that may be implemented to determine the intensity of an audience's biological response to a presentation (e.g., a sensory stimulus, media (e.g., content and/or advertisement), entertainment, etc.). The audience may include one or more subjects (e.g., a participant, a user, a panelist, a patient, a member of an audience, etc.) and the presentation may be any live or recorded, audio, visual or audio-visual material, for example. Disclosed example methods, apparatus/systems and articles of manufacture implement technique(s) that obtain biological response data, such as, for example, galvanic skin response (GSR) data, from a subject while the subject is exposed to a presentation and generate an intensity profile of the biological response to the presentation. As used herein, "intensity" means the strength of a measured biometric signal in response to a stimulus. An example technique disclosed herein includes identifying trough-to-peak instances (e.g., spikes, events) in the response data, ranking the trough-to-peak instances, and scoring the trough-to-peak instances based on the ranks. The score (e.g., a trough-to-peak score) to which a trough-to-peak instance is assigned depends on the magnitude of the increase in the response signal between the corresponding peak and trough. For example, a trough-to-peak instance may be scored based on a scale from 1 to 4. In this scale, 1 corresponds to a relatively low increase in the biometric signal and a 4 corresponds to a relatively large increase in the biometric signal. In other examples, other score ranges (e.g., scales, levels) having more or fewer discrete score values may be used (e.g., 0-3, 0-10, 5-30, etc.). In some examples, using a range having more score values (e.g., more discrete score values) enhances the ability to identify more subtle differences between the trough-to-peak values.

In some examples, score values are determined based on statistical boundaries. In some examples, the statistical boundaries are determined from a baseline test (e.g., a baseline video segment presented to the subject before the target presentation). For example, response data from a baseline test may be obtained, the trough-to-peak instances may be identified and measured, and the range (e.g., bins) of the trough-to-peak values may be used to establish boundaries between the different score value levels. The range of trough-to-peak values may be divided into percentiles (e.g., bins, increments, levels, etc.). In other words, percentiles of the trough-to-peak value range may be used to set boundaries for score levels. For example, the trough-to-peak value range may be split into quartiles. The first quartile may correspond to a range of lower trough-to-peak values, the second quartile may correspond to a range of lower to mid-level trough-to-peak values, the third quartile may correspond to a range of mid-level to high trough-to-peak values, and the fourth quartile may correspond to higher trough-to-peak values. Then, the trough-to-peak instances of the response data for the target presentation can be scored based on the score values of the respective quartiles.

In some examples, the scores (e.g., first scores, the trough-to-peak scores) are assigned to and/or associated with the troughs of the respective trough-to-peak instances (e.g., aligned with the time of the trough). In some examples, the scores of the trough-to-peak instances are assigned to windows of time to generate an intensity profile. In some examples, the windows have fixed lengths and are based on a sliding scale, which is disclosed in further detail herein. The windows may be assigned scores (e.g., second scores, window scores) based on the scores of the trough-to-peak instances occurring with the respective windows. In some examples, the windows are assigned scores corresponding to the highest scores of the trough-to-peak instance(s) occurring within the respective windows. An intensity profile may be generated based on the window scores. The intensity profile more accurately reflects the changes in the level of the response occurring during the presentation than the raw response data. In some examples, the intensity profiles from multiple subjects may be averaged and/or normalized by a maximum score value to yield a result in a desired range (e.g., 0-1). The intensity profiles can be used to identify elements (e.g., scenes, events, etc.) in the presentation that cause or elicit high and/or low levels of response and, thus, are linked to arousal, engagement, interest, etc. with the presentation.

Example methods, apparatus/systems and articles of manufacture disclosed herein can determine a measure of overall and/or moment-to-moment profile of intensity of the biological response. The intensity of the audiences' response to a presentation may indicate the level of engagement, focus, interest, etc. in the presentation. Therefore, the measure of intensity can be used to estimate the level to which an audience will be engaged by, like, dislike, etc. a same or similar presentation. In other words, by accurately measuring the intensity of the audience's response to a presentation, example methods, apparatus/systems and articles of manufacture disclosed herein can be used to better predict the audience's response(s) to another presentation. Additionally or alternatively, the example intensity profile may then be used to identify elements of the presentation that contribute to high levels of intensity and, thus, the effectiveness and success of the presentation.

Example methods, apparatus/systems and articles of manufacture disclosed herein can be used by directors, entertainment specialists, politicians, advertisers, media creators, marketers, distributors, etc. to accurately evaluate their presentation(s) prior to distribution/publication, for example, by objectively determining an audience's response to the presentation. Being able to estimate the overall impact of a given stimulus is important to, for example, promoters in identifying a target audience, corporate sponsors and advertisers for advertising purposes, clinicians for educating patients, teachers for educating and/or inspiring students, politicians for garnering votes, etc. Example methods, apparatus/systems and articles of manufacture disclosed herein may be used to determine which, if any, demographic group may find a particular presentation or portion of a presentation to be arousing to help determine its impact and make appropriate adjustments prior to general release. Additionally or alternatively, the measure of intensity of the sample population audience can be used to estimate the level to which the population, as a whole, may be aroused by (e.g., like, dislike, be indifferent to, attention captured by) the same presentation.

Example techniques disclosed herein are described in connection with galvanic skin response (GSR) data. Additionally or alternatively, the examples disclosed herein may likewise be applied to other types of biological responses such as heart rate, respiration rate, respiration state, body motion, eye tracking, functional magnetic resonance imaging (fMRI), electroencephalography (EEG), electrocardiograms (EKG), pupillary dilation, electrooculography (EOG), facial emotion encoding, reaction time and/or any other biologically based responses.

In general, galvanic skin response (GSR) or electrodermal activity (EDA) is the change in electrical properties occurring on the skin. GSR or EDA may also be referred to as electrodermal response (EDR), psychogalvanic reflex (PGR), skin conductance response (SCR) and skin conductance level (SCL). The signal can be used to capture the autonomic nerve responses as a parameter of the sweat gland function. In particular, the skin resistance varies with the state of the sweat glands in the skin. Sweating, which is controlled by the sympathetic nervous system, is indicative of psychological or physiological arousal. Therefore, measuring the conductance of the skin is an accurate measure of a subject's emotional and/or sympathetic responses. GSR can be measured using electrodes placed on the skin of the subject (e.g., on the palm, on the finger tips, etc.).

In some examples, the intensity measurements (with or without additional measures, such as synchrony) are used to determine engagement. The example intensity measurements may be used, for example, in place of the example intensity measurements disclosed in U.S. Pat. No. 8,296,172, titled "Methods and System for Determining Audience Response to a Sensory Stimulus," filed Sep. 5, 2007, which is incorporated by this reference in its entirety.

An example method disclosed herein includes accessing galvanic skin response (GSR) data obtained from a subject while exposed to a presentation. The GSR data includes a plurality of trough-to-peak instances. The example method includes generating, by executing an instruction with a processor, a GSR intensity profile by assigning trough-to-peak scores to corresponding ones of the trough-to-peak instances, defining a plurality of time windows, where each of the time windows commences a first time period after a preceding time window and each of the time windows has a duration of a second time period, where the second time period is greater than the first time period, and assigning window scores to corresponding ones of the time windows based on the trough-to-peak scores of the trough-to-peak instances occurring within the corresponding time windows to generate the GSR intensity profile. The example method also includes determining, by executing an instruction with the processor, an effectiveness of the presentation based on the window scores of the GSR intensity profile.

In some examples, the trough-to-peak instances include corresponding troughs and peaks, and the processor generates the GSR intensity profile by assigning the trough-to-peak scores to the troughs of the corresponding trough-topeak instances. In some examples, the method includes identifying the highest trough-to-peak score within the corresponding time windows, and the assigning of the window scores to the time windows includes selecting the highest trough-to-peak score occurring within the corresponding time windows as the corresponding window scores. In some examples, the time windows have corresponding start times and end times, and the assigning of the window scores to the time windows includes assigning the window scores to the start times of the corresponding time windows. In some examples, the GSR intensity profile is a graph of window scores over time.

In some examples, the subject is a first subject, and the example method includes averaging the GSR intensity profile of the first subject with a GSR intensity profile of a second subject to create an aggregated GSR intensity profile, normalizing the aggregated GSR intensity profile and determining the effectiveness of the presentation based on the normalized aggregated GSR intensity profile. In some examples, the method includes identifying trough-to-peak instances in baseline GSR data obtained from the subject during a baseline test, dividing the identified trough-to-peak instances into ranges and respectively assigning baseline values to the ranges, where the trough-to-peak scores of the trough-to-peak instances are based on corresponding ones of the baseline values. In some examples, a first time window of the plurality of time windows and a second time window of the plurality of time windows overlap in time.

In some examples, the method includes identifying, by executing an instruction with the processor, an element of the presentation corresponding to a level of GSR satisfying a threshold. In some such examples, the method further includes modifying the identified element of the presentation to no longer satisfy the threshold.

An example apparatus disclosed herein includes a presentation device to present a stimulus material to a subject, a galvanic skin response (GSR) sensor to gather GSR data from the subject while the subject is exposed to the stimulus material, a trough-to-peak scorer to assign trough-to-peak scores to corresponding trough-to-peak instances in the GSR data and a window generator to define a plurality of time windows. Each of the time windows commences a first time period after a preceding time window and each of the time windows has a duration of a second time period, where the second time period is greater than the first time period. The example apparatus also concludes a window scorer to assign window scores to corresponding ones of the time windows based on the trough-to-peaks scores of the trough-to-peak instances occurring within the corresponding windows, an intensity profile generator to generate a GSR intensity profile based on the window scores and an effectiveness determiner to determine an effectiveness of the presentation based on the window scores of the GSR intensity profile.

In some examples, the trough-to-peak instances include corresponding troughs and peaks, and the window scorer is to assign the trough-to-peak scores to the troughs of the corresponding trough-to-peak instances. In some examples, the window scorer is to assign the window scores to the corresponding time windows by selecting the highest trough-to-peak score occurring within the corresponding time windows as the corresponding window scores. In some examples, the time windows have corresponding start times and end times, and the window scorer is to assign the window scores to the time windows by assigning the window scores to the start times of the corresponding time windows. In some examples, the GSR intensity profile is a graph of the window scores over time.

In some examples, the subject is a first subject, and the intensity profile generator is to average the GSR intensity profile of the first subject with a GSR intensity profile of a second subject to create an aggregated GSR intensity profile and normalize the aggregated GSR intensity profile. In such an example, the effectiveness of the presentation is based on the normalized aggregated GSR intensity profile.

In some examples, the apparatus includes a trough-to-peak identifier to identify trough-to-peak instances in baseline GSR data obtained from the subject during a baseline test and a score value determiner to divide the identified trough-to-peak instances into ranges and respectively assign baseline values to the ranges. In some such examples, the trough-to-peak scores of the trough-to-peak instances are based on corresponding ones of the baseline values. In some examples, a first time window of the plurality of time windows and a second time window of the plurality of time windows overlap in time.

In some examples, the apparatus includes a presentation modifier to identify an element of the presentation corresponding to a level of GSR satisfying a threshold. In some such examples, the presentation modifier is to modify the identified element of the presentation to no longer satisfy the threshold.

Disclosed herein is an example tangible machine readable storage medium having instructions that, when executed, cause a machine to at least assign trough-to-peak scores to corresponding trough-to-peak instances in galvanic skin response (GSR) data. The GSR data is obtained from a subject while the subject is exposed to a presentation. The example instructions, when executed, cause the machine to define a plurality of time windows, where each of the time windows commences a first time period after a preceding time window and each of the time windows has a duration of a second time period, where the second time period greater than the first time period. The example instructions, when executed, also cause the machine to generate a GSR intensity profile by assigning window scores to corresponding ones of the time windows based on the trough-to-peaks scores of the trough-to-peak instances occurring within the corresponding time windows and determine an effectiveness of the presentation based on the window scores of the GSR intensity profile.

In some examples, the trough-to-peak instances include corresponding troughs and peaks, and the instructions, when executed, cause the machine to generate the GSR intensity profile by assigning the trough-to-peak scores to the troughs of the corresponding trough-to-peak instances. In some examples, the instructions, when executed, further cause the machine to identify the highest trough-to-peak score within the corresponding time windows and assign the window scores to the time windows by selecting the highest trough-to-peak score occurring within the corresponding time windows as the corresponding window scores. In some examples, the time windows have corresponding start times and end times, and the instructions, when executed, cause the machine to assign the window scores to the time windows by assigning the window scores to the start times of the corresponding time windows. In some examples, the GSR intensity profile is a graph of the window scores over time.

In some examples, the subject is a first subject, and the instructions, when executed, further cause the machine to average the GSR intensity profile of the first subject with a GSR intensity profile of a second subject to create an aggregated GSR intensity profile, normalize the aggregated GSR intensity profile and determine the effectiveness of the presentation based on the normalized aggregated GSR intensity profile. In some examples, the instructions, when executed, further cause the machine to identify trough-to-peak instances in baseline GSR data obtained from the subject during a baseline test, divide the identified trough-to-peak instances into ranges and respectively assign baseline values to the ranges, where the trough-to-peak scores of the trough-to-peak instances are based on the corresponding ones of the baseline values. In some examples, a first time window of the plurality of time windows and a second time window of the plurality of time windows overlap in time.

In some examples, the instructions, when executed, further cause the machine to identify an element of the presentation corresponding a level of GSR satisfying a threshold. In some such examples, the instructions, when executed, further cause the machine to modify the identified element of the presentation to no longer satisfy the threshold.

FIG. 1 illustrates an example intensity measurement system 100 for measuring a level of intensity of a biological response of a subject 102 responding to a stimulus. The example system 100 of FIG. 1 includes a sensor 104 coupled to the subject 102. The sensor 104 of the illustrated example is a GSR sensor that obtains biometric data (e.g., GSR data) while the subject 102 is exposed to a stimulus (e.g., a presentation, media, content, etc.). The sensor 104 may include one or more electrodes. In the illustrated example, the sensor 104 is coupled to a hand of the subject 102. However, in other examples, the sensor 104 may be attached to other areas of the body and/or may include multiple sensors (e.g., multiple electrodes) attached to other areas of the body. Additionally or alternatively, in some examples other types of sensors (e.g., a camera, an EEG electrode, etc.) may be used to gather biometric data representative of other types of biological responses, such as, for example, heart rate, respiration rate, brain waves, pupillary dilation, facial motion, etc.

In the illustrated example, the subject 102 is exposed to a presentation from a presentation device 106. In the illustrated example, the presentation device 106 is implemented as a television (TV), and the presentation is a television broadcast or downloaded (e.g., streamed) program. In other examples, the presentation 106 may be any live or recorded, passive or interactive audio, visual, or audio-visual presentation. The presentation device 106 may include, for example, a TV, a computer monitor, a radio, a smart phone, a tablet, a gaming console, a projection system, a speaker, a streaming device, and/or any other display or presentation device. For example, the presentation may be a live or recorded viewing of a soccer game on a TV. In another example, the presentation may be a live viewing of the soccer game while the subject 102 is at the stadium. In another example, the presentation may be a picture on a computer screen or in a document (e.g., a newspaper) that the subject 102 is viewing.

While the subject 102 is exposed to the presentation, a monitoring station 108 receives and records the GSR data obtained by the sensor 104. In the illustrated example, the sensor 104 is communicatively coupled to the monitoring station 108 via a wire. In other examples, the sensor 104 wirelessly communicates the GSR data to the monitoring station 108. In some examples, information relating to the timing of the presentation is received by the monitoring station 108. In the illustrated example, the presentation device 106 is communicatively coupled to the monitoring station 108 via a wire. In other examples, the presentation device 106 wirelessly communicates with the monitoring station 108. The monitoring station 108 may be remote from the subject 102 and/or the presentation device 106. In other words, the GSR data obtained by the sensor 104 and/or the presentation information may be obtained offsite and transmitted to the monitoring station 108 in real time or after the subject 102 has been exposed to the presentation. In some examples, the presentation is a live viewing of an event (e.g., a soccer game) and the presentation device 106 is a camera recording the event. In such an example, the collected GSR data is transmitted to the monitoring station 108 with corresponding images (and/or timing information) collected by the camera.

In the illustrated example, the monitoring station 108 includes a monitor or display 110, such as a computer monitor. However, in other examples, the monitoring station 108 may not include a display. The example monitoring station 108 of FIG. 1 includes a database 114, a trough-to-peak (T2P) identifier 116, a T2P value determiner 118, a score value determiner, a T2P scorer 120, a window generator 122, a window scorer 124, an intensity profile generator 126, an effectiveness determiner 128 and a presentation modifier 130, the structures and operations of which are described in connection with the following examples illustrated in FIGS. 2-7.

Figure 2:
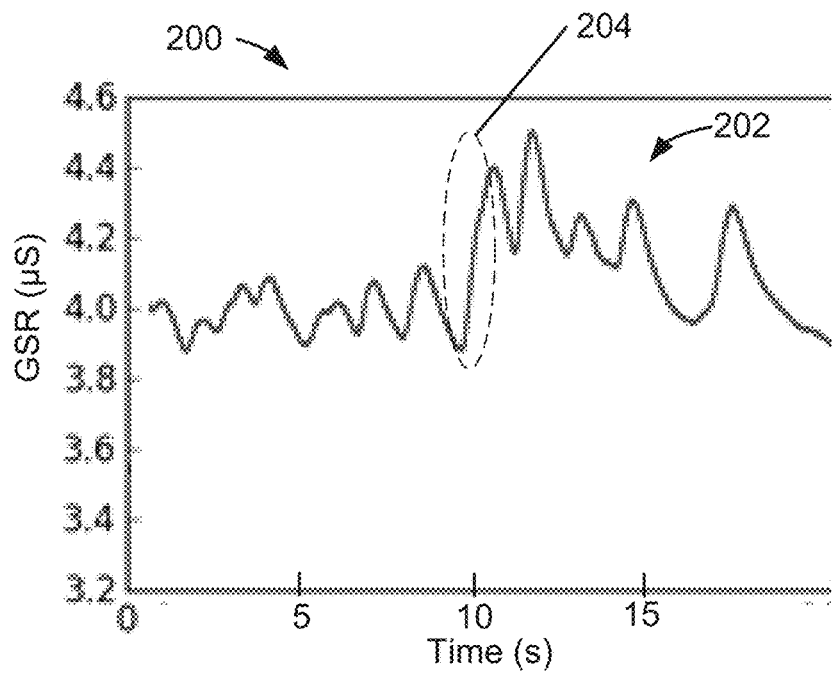
FIG. 2 is an example graph of galvanic skin response (GSR) data obtained from an example baseline test using the example intensity measurement system of FIG. 1.

In some examples, prior to analyzing the GSR data obtained from the subject 102, baseline GSR data is obtained and analyzed by the monitoring station 108 to determine score values (e.g., baseline values) for use when ranking the GSR data from the target or desired presentation. FIG. 2 shows an example GSR graph 200 displaying example baseline GSR data 202 obtained from the subject 102 during an example baseline presentation. The baseline presentation may be a test or sample presentation presented to the subject 102. The baseline presentation may be a shortened version of the target presentation or an entirely different presentation. In some examples, the baseline presentation is intended to elicit or evoke the whole range of a subject's possible responses to a stimulus. In other examples, the baseline is used to determine a subset of subject response levels. The GSR graph 200 may be displayed on the monitor 110, for example. The monitoring station 108 obtains the GSR data 202 from the subject 102 while the subject 102 is exposed to the baseline test. The GSR data 202 may be recorded in the database 114, for example. The Y-axis of the GSR graph 200 represents the strength of the signal gathered by the sensor 104, and the X-axis of the GSR graph 200 represents time in seconds. In the illustrated example, the Y-axis of the GSR graph 200 represents the conductance of the skin measured by the sensor 104 and shows the strength of the GSR signal. The Y-axis may be represented, for example, in micro-Siemens (μS), which is a unit of electrical conductance. In other examples, the Y-axis includes unit-less numbers that identify the relative strength of a response. In other examples, the GSR data 202 may be measured and/or displayed in different parameters or units (e.g., kilo-Ohms) depending on the type of biometric sensor device.

As illustrated in the GSR graph 200, the GSR data 202 includes a plurality of trough-to-peak instances (e.g., spikes, events, etc.). A rise in the GSR data 202 is often indicative of arousal, which in this context is caused by the presentation. The T2P identifier 116 identifies the T2P (trough-to-peak) instances in the GSR data 202, taken from a trough to a subsequent peak. An example T2P instance 204 is circled in the GSR graph 200. The GSR data 202 may include more or fewer T2P instances depending on the subject's response.

Figure 3:
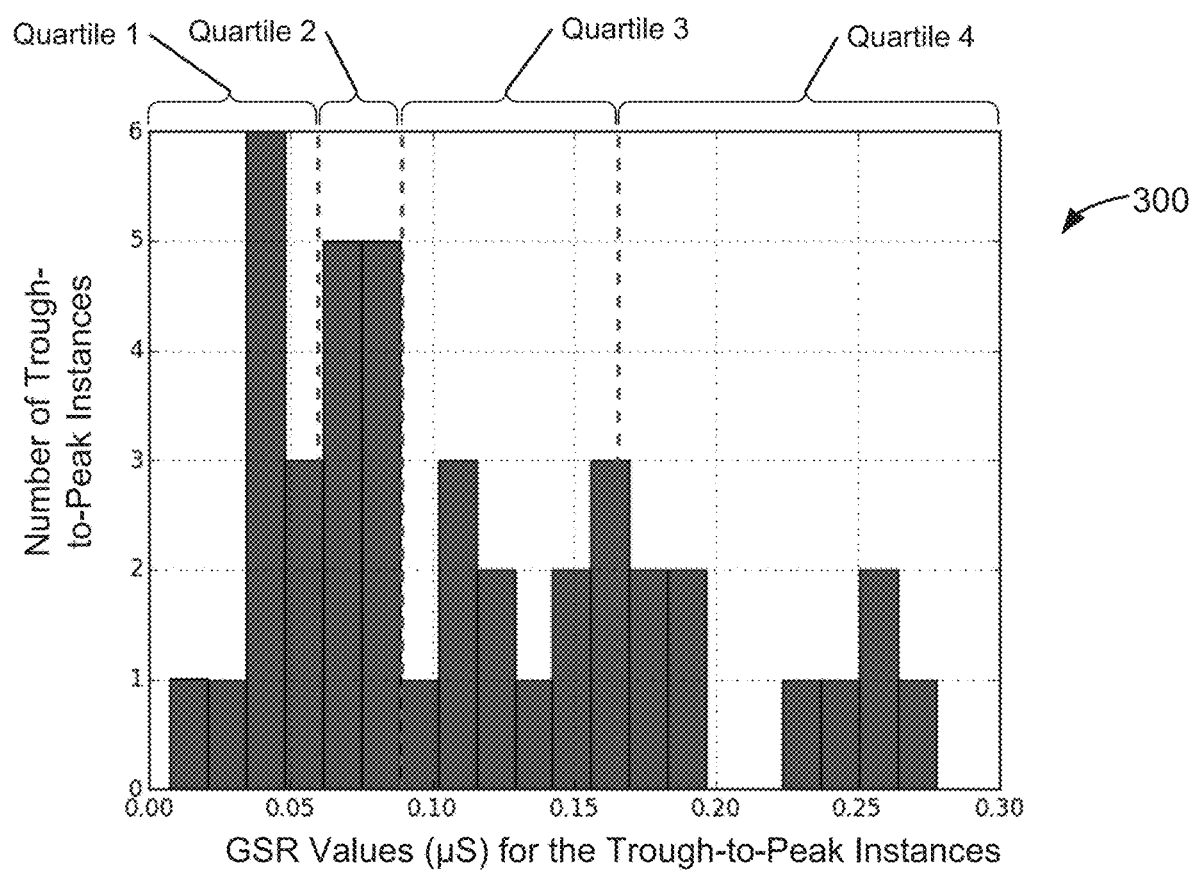
FIG. 3 is an example histogram of example trough-to-peak instances of the example GSR data from the example baseline test of FIG. 2 generated using the example intensity measurement system of FIG. 1.

The T2P value determiner 118 measures the change in GSR from the trough to the peak of the respective T2P instances. After the T2P value determiner 118 determines the values or levels of rise (e.g., the amplitude changes) in the GSR data 202, the score value determiner 119 divides the values into percentiles (e.g., bins) and assigns certain score values (e.g., baseline values) to each of the percentiles. For example, FIG. 3 shows an example histogram 300 of the T2P instances gathered during an example baseline presentation. The Y-axis of the histogram 300 represents the number of T2P instances and the X-axis of the histogram 300 represents the corresponding GSR values (trough-to-peak values) for the T2P instances. In the illustrated example, the values of the T2P instances are be divided into ranges represented by Quartiles 1, 2, 3 and 4, as shown in FIG. 3. Each quartile may be assigned a specific score value. For example, Quartile 1 may be assigned a score value of 1, Quartile 2 may be assigned a score value of 2, Quartile 3 may be assigned a score value of 3, and Quartile 4 may be assigned a score value of 4. Then, when measuring the GSR data from the subject 102 during a target presentation, a T2P instance having a GSR value within Quartile 1 (e.g., 0.00-0.06 μS) may be assigned a score of 1, a T2P instance having a GSR value within Quartile 2 (e.g., 0.06-0.09 μS) may be assigned a score of 2, a T2P instance having a GSR value within Quartile 3 (e.g., 0.09-0.16 μS) may be assigned a 3, and a T2P instance having a GSR value within Quartile 4 (e.g., 0.16-0.30 μS) may be assigned a score of 4. In other examples, the T2P values may be divided or defined into other percentiles (e.g., thirds, halves, etc.) and/or based on other statistical boundaries. In other examples, other score values may be assigned to the percentiles or levels. For example, Quartile 1 may be assigned a score value of 0, Quartile 2 may be assigned a score value of 1, Quartile 3 may be assigned a score value of 2 and Quartile 4 may be assigned a score value of 3. The histogram 300 may be displayed on the monitor 110, for example.

Figure 4:
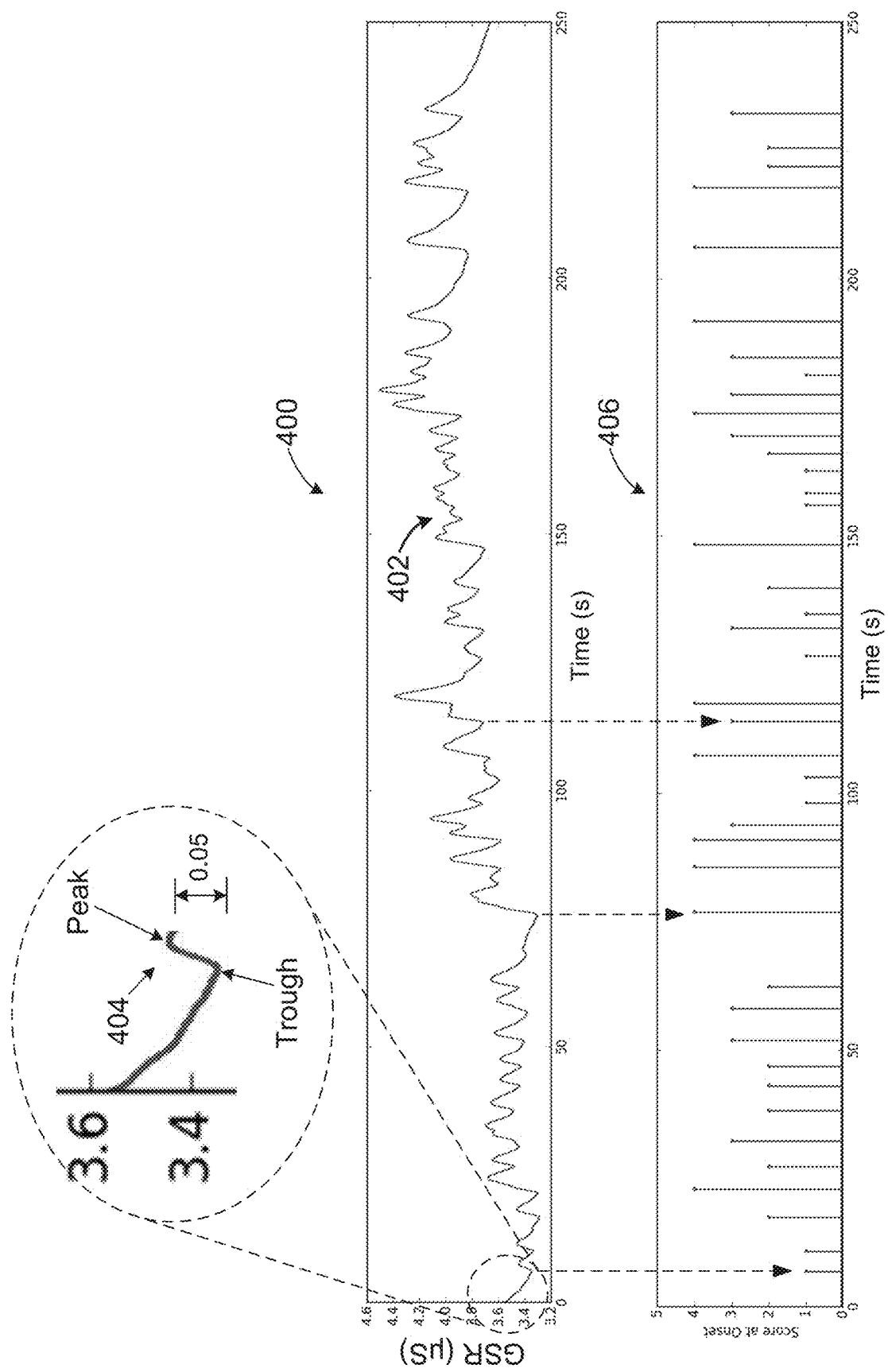
FIG. 4 includes two example graphs generated using the example intensity measurement system of FIG. 1. The first graph illustrates example GSR data obtained by the example intensity measurement system of FIG. 1 and the second graph illustrates example scores assigned to example trough-to-peak instances occurring in the example GSR data of the first graph.

FIG. 4 illustrates an example GSR graph 400 displaying example GSR data 402 (e.g., a GSR timeline) obtained while the subject 102 is exposed to the presentation (e.g., the target presentation). The Y-axis of the GSR graph 400 represents the strength of the signal gathered by the sensor 104, and the X-axis of the GSR graph 400 represents time in seconds. In the illustrated example, the Y-axis is the resistance in μS. However, in other examples, the GSR values may be measured in different parameters. As shown in the illustrated example of FIG. 4, the GSR data 402 includes a plurality of T2P instances. The GSR graph 400 may be displayed on the monitor 110, for example. After or while the GSR data 402 is being obtained (and/or recorded), the T2P identifier 116 identifies the T2P instances in the GSR data 402, including, for example, the points in time corresponding to the troughs (i.e., the lowest point of the GSR value before an increase) and the peaks (i.e., the highest point in the GSR value before a decrease). The T2P value determiner 118 measures the values or levels of increase for the T2P instances (e.g., the change in μS from the trough to the peak).

Once the values or levels of increase are determined for the T2P instances, the T2P scorer 120 determines scores for the T2P instances based on the values. In other words, the T2P scorer 120 ranks the T2P instance based on the level or rise of GSR data 402. In some examples, the scores are based on the score values determined from a baseline test, such as shown in the histogram 300 of FIG. 3. For example, a first T2P instance 404 is identified in the GSR data 402. The increase in GSR value between the trough and the peak is about 0.05 μS. A GSR increase of 0.05 μS corresponds to Quartile 1 of the histogram 300 in FIG. 3. As such, the first T2P instance 404 is assigned a score of 1. In some examples, the scores of the T2P instances are plotted in a score graph 406, as illustrated in FIG. 4. In the illustrated example, the score of the first T2P instance 404 is assigned to or associated with the time corresponding to the trough of the first T2P instance 404. In some instances, GSR has a delayed reaction to a stimulus. As such, by scoring the first T2P instance 404 at the trough, the score is more accurately aligned with the element(s) in the presentation that caused or elicited the corresponding rise or spike in GSR signal. In other examples, the score can be assigned to another time or point of the first T2P instance 404. The T2P identification, value determination and score determination may be repeated for each of the T2P instances in the GSR data 402. The example score graph 406 illustrates all of the scores of the T2P instances occurring in the GSR data 402. As illustrated, the scores of the respective T2P instances are assigned to or associated with the time of the troughs (e.g., the time of the lowest point before a rise in GSR) of the respective T2P instances.

Figure 5:
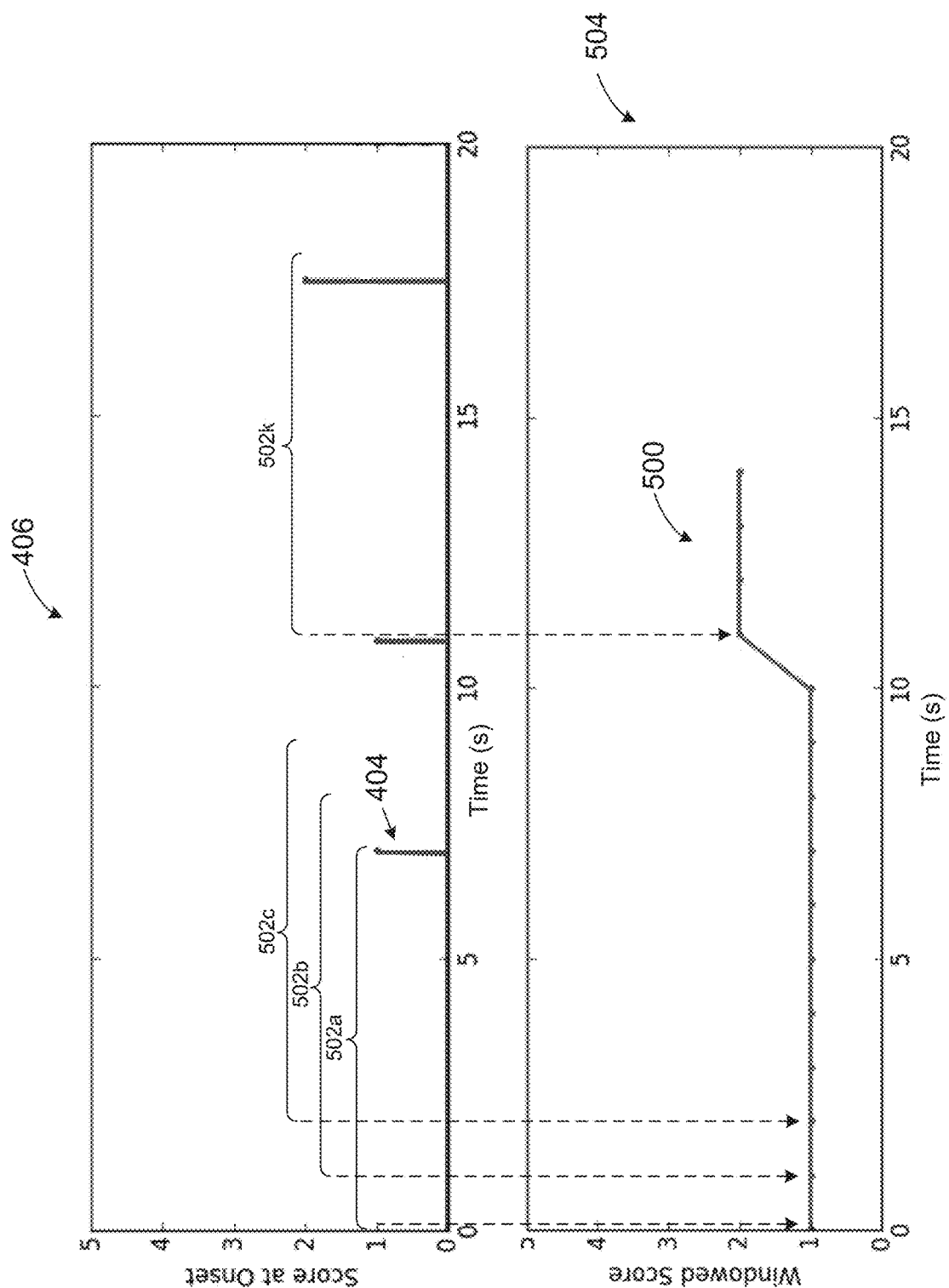
FIG. 5 includes two example graphs generated using the example intensity measurement system of FIG. 1. The first graph is an enlarged view of the first example graph from FIG. 4 and illustrates example windows and the second graph illustrates an example intensity profile for the presentation.

After the scores for the T2P instances are determined, the example monitoring station 108 uses the scores to assign scores to windows (e.g., time windows, time slots, events, etc.) to generate an intensity profile. FIG. 5 illustrates an enlarged view of the example score graph 406 from 0 seconds to 20 seconds and a corresponding GSR intensity profile 500 (as discussed in further detail herein).

The window generator 122 defines a plurality of windows. In some examples, the windows are defined by a fixed time length using a sliding scale. In other words, instead of having fixed consecutive windows, the windows are defined using a sliding scale. For example, a window $T_W$ of fixed time length $T_L$ is shifted along the GSR data 402 in increments of $T_S$. For instance or time shift i, the time window $T_{W,i}$ of interest is defined by time T given in Equation 1.

$$T_S \times i \leq T \leq T_S \times i + T_L \qquad \text{Equation 1.}$$

The example windows may be defined by any length of time $T_L$ and any increment $T_S$. For example, in the illustrated example of FIG. 5, a fixed time length $T_L$ of 7 seconds with an increment $T_S$ of 1 second is implemented. Therefore, a first window 502a occurs or spans from T=0 s to T=7 s, a second window 502b occurs from T=1 s to T=8 s, a third window 502c occurs from T=2 s to T=9 s, and so forth. Therefore, the example window generator 122 defines a plurality of windows, where each of the time windows commences a first time period (e.g., increment $T_S$) after a preceding time window and each of the time windows has a duration of a second time period (e.g., fixed time length $T_L$), and the second time period is greater than the first time period. For example, the fixed time length $T_L$ of 7 s is greater than the increment $T_S$ of 1 s. As such, the time windows overlap. For example, in the illustrated example of FIG. 5, the first window 502a partially overlaps in time with the second window 502b (e.g., from T=1 s to T=7 s).

After the windows are defined, the window scorer 124 assigns scores to the respective windows, and the intensity profile generator 126 generates the GSR intensity profile 500 as illustrated in a windowed score graph 504 of FIG. 5. The Y-axis of the windowed score graph 504 represents the scores of the windows and the X-axis of the windowed score graph 504 represents time in seconds.

For example, in this first window 502a, the highest T2P score is of the first T2P instance 404 and has a score of 1. As such, the window scorer 124 assigns the first window 502a a score of 1, as illustrated in the GSR intensity profile 500. In the illustrated example, the score of the first window 502a is associated with the time corresponding to the beginning of the first window 502a (i.e., 0 s). In the second window 502*b*, the highest T2P score is of the first T2P instance 404 and has a score of 1. As such, the window scorer 124 assigns the second window 502*b* a score of 1, as illustrated in the GSR intensity profile 500. In the illustrated example, the score of the second window 502*b* is associated with the time corresponding to the beginning of the second window 502*b* (i.e., 1 s). In the third window 502*c*, the highest T2P score is of the first T2P instance 404 and has a score of 1. As such, window scorer 124 assigns the third window 502*c* a score of 1, as illustrated in the GSR intensity profile 500. In the illustrated example, the score of the third window 502*c* is associated with the time corresponding to the beginning of the third window 502*c* (i.e., 2 s). The window scorer 124 continues to assign scores to each of the windows of based on the highest scores of the T2P instance(s) occurring in the respective windows. In some examples, the window scorer 124 compares the scores of the T2P instance(s) to determine the highest scores in each of the windows and selects the highest scores occurring within the respective windows.

In the illustrated example, an eleventh window 502*k* occurs at T=11 s to T=18 s. In this window, the highest T2P score is of a T2P having a score of 2. As such, the eleventh window 502*k* is assigned a score of 2, as illustrated in the GSR intensity profile 500. In the illustrated example, the score of the eleventh window 502*k* is associated with the time corresponding to the beginning of the eleventh window 502*k* (i.e., 11 s). In some examples, if a window includes multiple scores of multiple T2P instances, the highest score occurring in the window is assigned to the window. In other examples, other ones of the scores may be assigned to the windows (e.g., based on the lowest T2P score within the window, based on an average of all the T2P scores within the window, based on a sum of all the T2P scores within the window, etc.). The intensity profile generator 126 uses the window scores to create the GSR intensity profile 500. The GSR intensity profile 500 may be displayed on the monitor 110, for example.

Therefore, the GSR intensity profile 500 is generated by determining scores every time increment $T_S$, where the scores are based on windows of fixed time length $T_L$ starting at $T_{S,I}$ and spanning the fixed time length $T_L$. For example, at T=0, a score is generated based on a window defined by T=0 to T=7, at T=1, a score is generated based on a window defined by T=1 to T=8, and so forth. This example technique employs overlapping windows of time, which are based on a sliding scale rather than having consecutive time windows. By overlapping the windows (instead of having consecutive windows), a profile is generated that has a higher resolution (e.g., more granular) and, thus, more accurately portraying the intensity of the biological response corresponding to the presentation. In other words, the scores of the profile are based on upcoming T2P instances (which are scored at the troughs), and the time after the troughs of the T2P instances are not assigned the score for the T2P instance. The GSR intensity profile 500 emphasizes or more accurately reflects the time portions before a stimulating event or time in the presentation. As such, the producer(s) of the presentation can more easily and effectively analyze the results of the presentation.

In the illustrated example, the scores of the respective T2P instances are based on the statistical boundaries defined by the baseline test, as illustrated in FIGS. 2 and 3. However, in other examples, score values may be determined in other manners. For example, a histogram of the T2P instances of the GSR data 402 may be used to determine score values. In other examples, the score values may be set or provided by a third party entity. In other examples, the score values may be pre-established based on multiple baseline tests from one or more subjects.

Figure 6:
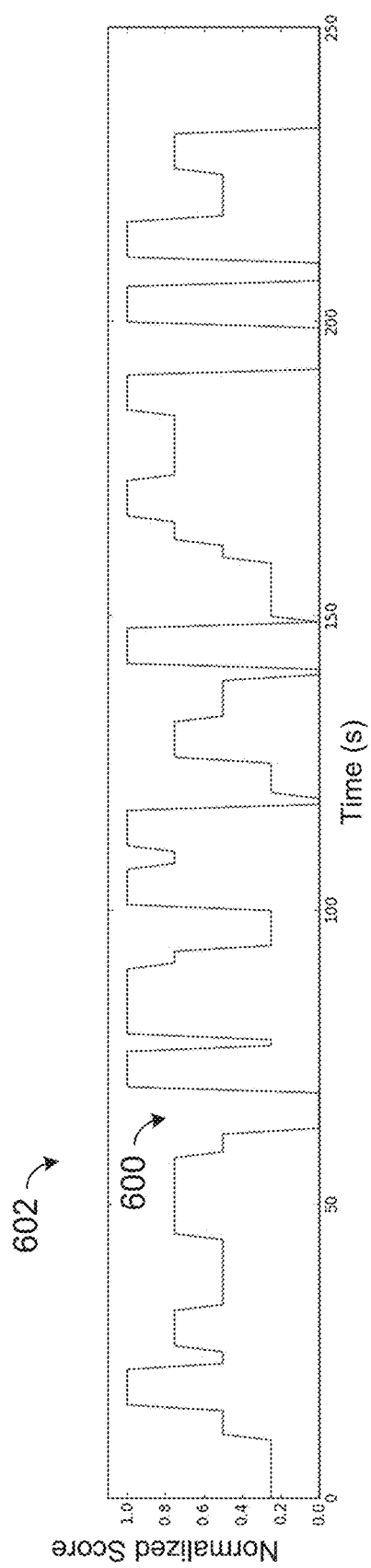
FIG. 6 is an example graph showing a normalized view of the example intensity profile of FIG. 5 generated using the example intensity measurement system of FIG. 1.

In some examples, after the GSR intensity profile 500 is generated, the intensity profile generator 126 may normalize or rescale the GSR intensity profile 500 (e.g., from 0 to 1). FIG. 6 illustrates an example normalized GSR intensity profile 600 in an example graph 602. In some examples, multiple GSR intensity profiles from multiple subjects may be averaged to produce an aggregated GSR intensity profile 700, as illustrated in the example graph 702 of FIG. 7. For example, the scores of each members GSR intensity profile at every $T_S$ may be averaged to produce the aggregated GSR intensity profile 700. In some examples, each subject's GSR intensity profile is normalized first, and then GSR intensity profiles are averaged. In other examples, the GSR intensity profiles are averaged first, and then the aggregated GSR intensity profile is normalized (e.g., by maximum score value) to yield a result from 0-1 range, 0 being no response activity (e.g., low intensity) and 1 being maximum response activity (e.g., high intensity).

Figure 7:
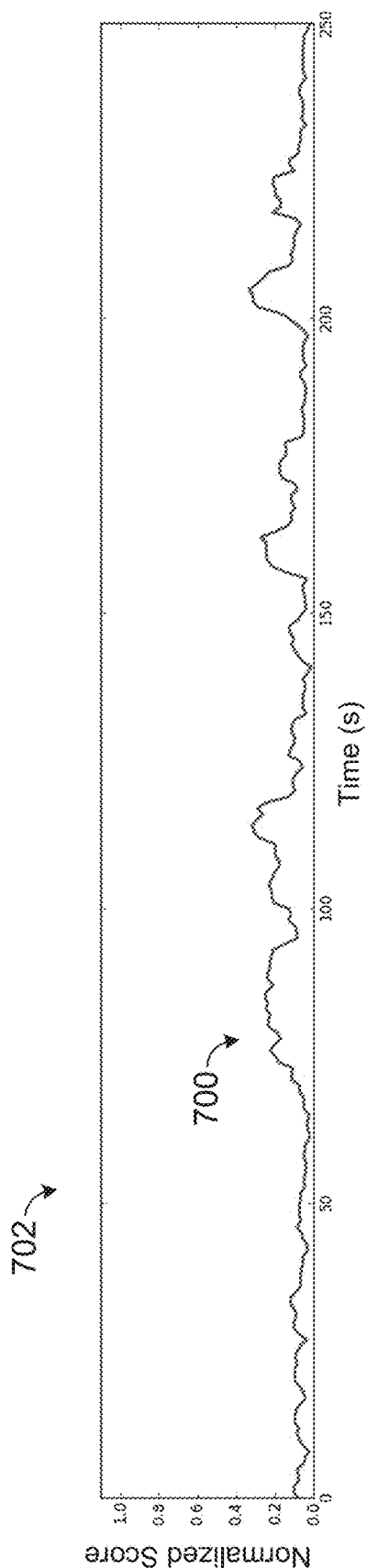
FIG. 7 is an example graph showing an example aggregated intensity profile generated using the example intensity measurement system of FIG. 1.

In some examples, the monitoring station 108 can generate a report of the GSR intensity profile 500 (FIG. 5) for one or more subjects, the normalized GSR intensity profile (FIG. 6) for one or more subjects, and/or the aggregated GSR intensity profile 700 (FIG. 7). The report may identify the times in the presentation that correlate to increased and/or decreased GSR intensity and, thus, are indicative of increased or decreased arousal to the presentation.

In some examples, the aggregated GSR intensity profile 700 may be combined (e.g., aggregated) with biometric response data from one or more other biometric response measurement device(s) 132 (FIG. 1). The biometric response data may include, for example, heart rate, heart rate variability, vagal tone, respiration data, body movement data, measures of facial muscle movement/expression, body temperature data, near body temperature data, facial and body thermography imaging, EEG, EKG, facial EMG, fMRI, eye movement, etc. The measurement device(s) 132 may be, for example, an eye tracking device (e.g., a camera) for monitoring eye fixation location and/or fixation duration, one or more EEG electrodes coupled to the head of the subject 102 for obtaining EEG signals, one or more EKG electrodes coupled to the subject 102 for obtaining EKG signals, etc. In some examples, the example monitoring station 108 obtains the biometric response data and combines it with the aggregated GSR intensity profile 700 to generate an engagement profile. The engagement profile may be used to identify elements in the presentation that correlate to increased and/or decreased engagement with the presentation. In some examples, the aggregated GSR intensity profile 700 and/or the engagement profile may be used to determine the success of one or more portions (e.g., scenes, events, etc.) of the presentation and/or the overall presentation, to determine the effectiveness of one or more portions of the presentation and/or the overall presentation, etc.

For example, the effectiveness determiner 128 may determine an effectiveness of the presentation based on the aggregated GSR intensity profile 700 (e.g., based on the scores of the windows 502*a*-502*n*) by comparing a number of times the score of the aggregated GSR intensity profile 700 meets (e.g., exceeds) an intensity threshold within a period of time (e.g., 50 seconds). Additionally or alternatively, the effectiveness may be based on a duration of the instance(s) of the GSR intensity meets the intensity threshold. In another example, the effectiveness determiner 128 may determine an effectiveness of a portion or element of the presentation based on the aggregated GSR intensity profile 700 by comparing the score(s) during the element to an intensity threshold. For example, if the score(s) during the element (e.g., during a scene occurring at 10 s-20 s) of the presentation is above the threshold, the element may be identified as eliciting high levels of response (e.g., arousal), and if the score(s) during the element of the presentation are below the threshold, the element may be identified as eliciting low levels of response. In some examples, the effectiveness determiner 128 and/or the presentation modifier 130 may identify elements of the presentation that can be modified to enhance the effectiveness of the presentation (e.g., by removing or replacing the elements causing low levels of response and/or repeating or highlighting elements that cause high levels of response). For example, the presentation modifier 130 may automatically select between two alternative presentation segments (e.g., scenes, events, etc.) based on the effectiveness of one or both of the presentation segments. In some examples, the effectiveness determiner 128 and/or the presentation modifier 130 may identify an element of a presentation corresponding to a level of GSR satisfying a threshold, and the presentation modifier 130 may modify the element to no longer satisfy the threshold. For example, the effectiveness determiner 128 and/or the presentation modifier 130 may identify that an element of that fails to satisfy or meet a threshold (e.g., music in a scene in a horror film does not cause the desired biological response indicative of anxiety or fear), and the presentation modifier 130 modifies the element to cause the desired response (e.g., to cause the desired biological response). For example, the threshold may be a low threshold or high threshold, and if the element satisfies the low threshold (e.g., falls below the low threshold) or the high threshold (e.g., exceeds the high threshold), the presentation modifier 130 modifies the element to no longer satisfy the threshold (e.g., by replacing the element with an alternate element that causes increased GSR response that brings the response above the low threshold, or by replacing the element with an alternate element that causes decreased GSR response that brings the response below the high threshold). In some examples, the effectiveness determiner 128 and/or the presentation modifier 130 may configure the output of a device such as a cell phone color scheme in response to the effectiveness.

In some examples, the aggregated GSR intensity profile 700 and/or the engagement profile for a presentation may be ranked among other GSR intensity profiles and/or engagement profiles for other presentations (e.g., stored in the database 114). In some examples, the effectiveness determiner 128 may determine an effectiveness of the presentation based on the ranking of the aggregated GSR intensity profile 700 among the other GSR intensity profiles.

While an example manner of implementing the system 100 of FIG. 1 is illustrated in FIG. 1, one or more of the elements, processes and/or devices illustrated in FIG. 1 may be combined, divided, re-arranged, omitted, eliminated and/or implemented in any other way. Further, the example monitoring station 108, the example database 114, the example T2P identifier 116, the example T2P value determiner 118, the example score value determiner 119, the example T2P scorer 120, the example window generator 122, the example window scorer 124, the example intensity profile generator 126, the example effectiveness determiner 128, the example presentation modifier 130 and/or, more generally, the example system 100 of FIG. 1 may be implemented by hardware, software, firmware and/or any combination of hardware, software and/or firmware. Thus, for example, any of the example monitoring station 108, the example database 114, the example T2P identifier 116, the example T2P value determiner 118, the example score value determiner 119, the example T2P scorer 120, the example window generator 122, the example window scorer 124, the example intensity profile generator 126, the example effectiveness determiner 128, the example presentation modifier 130 and/or, more generally, the example system 100 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example monitoring station 108, the example database 114, the example T2P identifier 116, the example T2P value determiner 118, the example score value determiner 119, the example T2P scorer 120, the example window generator 122, the example window scorer 124, the example intensity profile generator 126, the example effectiveness determiner 128, and/or the example presentation modifier 130 is/are hereby expressly defined to include a tangible computer readable storage device or storage disk such as a memory, a digital versatile disk (DVD), a compact disk (CD), a Blu-ray disk, etc. storing the software and/or firmware. Further still, the example system 100 of FIG. 1 may include one or more elements, processes and/or devices in addition to, or instead of, those illustrated in FIG. 1, and/or may include more than one of any or all of the illustrated elements, processes and devices.

Figure 8A:
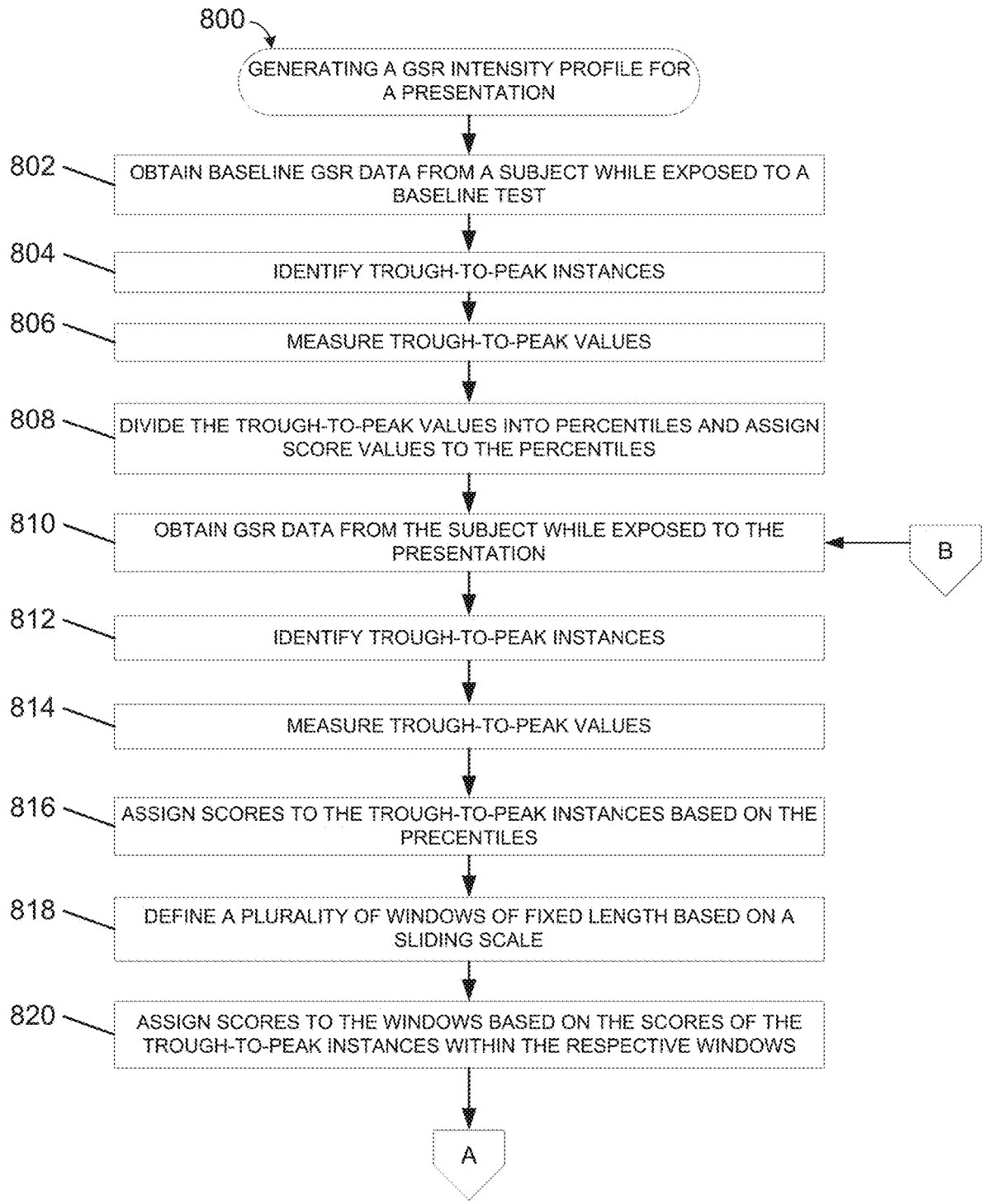
FIGS. 8A and 8B are flowcharts representative of example machine executable instructions, which may be executed to implement the example intensity measurement system FIG. 1.
Figure 8B:
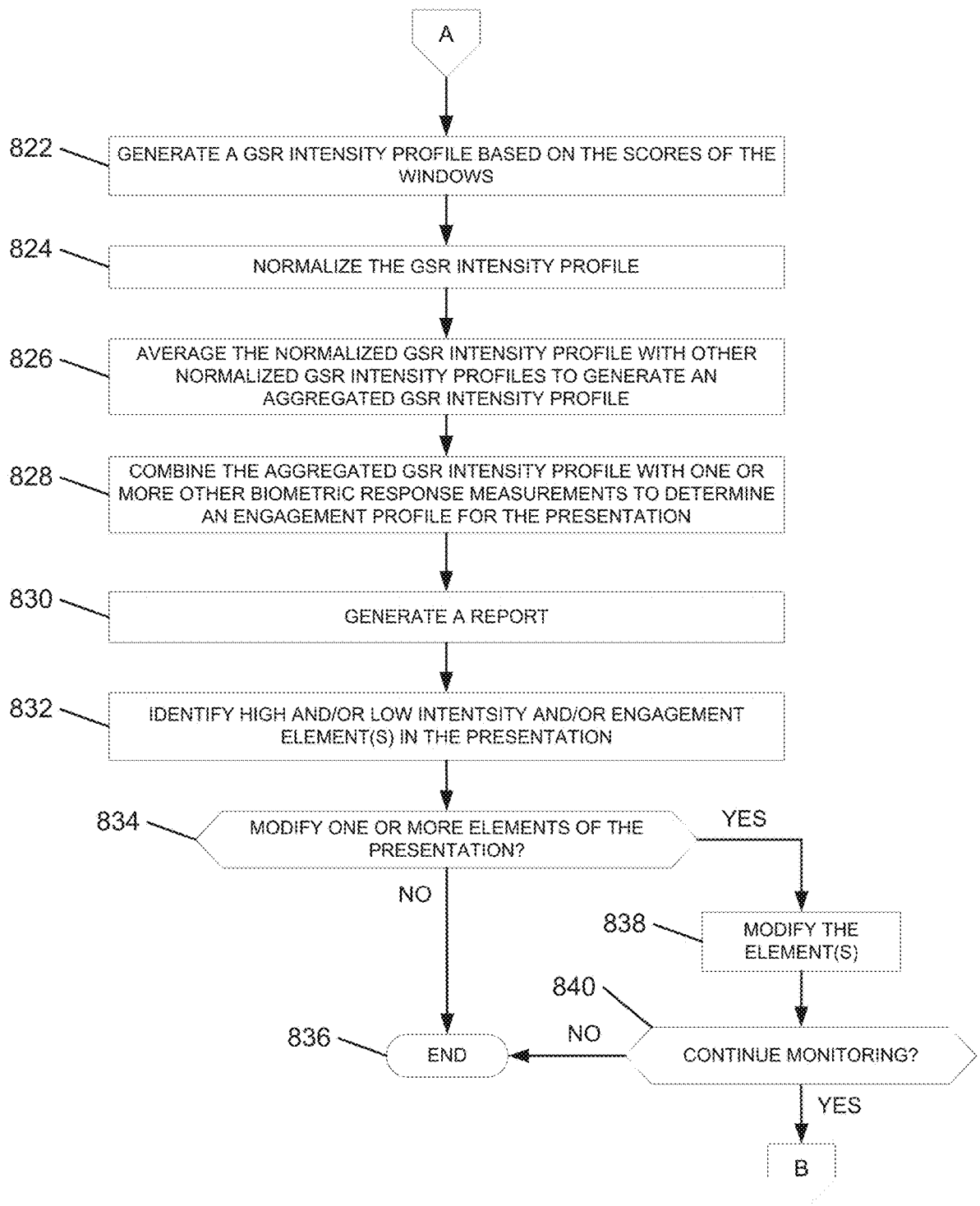

A flowchart representative of example machine readable instructions for implementing the system 100 of FIG. 1 is shown in FIGS. 8A and 8B. In this example, the machine readable instructions comprise a program for execution by a processor such as the processor 912 shown in the example processor platform 900 discussed below in connection with FIG. 9. The program may be embodied in software stored on a tangible computer readable storage medium such as a CD-ROM, a floppy disk, a hard drive, a digital versatile disk (DVD), a Blu-ray disk, or a memory associated with the processor 912, but the entire program and/or parts thereof could alternatively be executed by a device other than the processor 912 and/or embodied in firmware or dedicated hardware. Further, although the example program is described with reference to the flowchart illustrated in FIGS. 8A and 8B, many other methods of implementing the example system 100 may alternatively be used. For example, the order of execution of the blocks may be changed, and/or some of the blocks described may be changed, eliminated, or combined.

As mentioned above, the example process of FIGS. 8A and 8B may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example process of FIGS. 8A and 8B may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

FIGS. 8A and 8B are a flowchart representative of example machine readable instructions 800 that may be executed to generate a GSR intensity profile for a presentation. While the instructions 800 of FIGS. 8A and 8B are described in connection GSR data, the example instructions 800 can likewise be applied to other biological responses (e.g., heart rate, respiration rate, eye tracking, EEG, etc.) in addition to or as an alternative to GSR data.

In some examples, prior to analyzing a subject's GSR, baseline data is obtained. In some examples, the baseline data is determined based on a baseline test, which may be a test or sample presentation presented to the subject (e.g., before or after the obtaining the subject's GSR to a target presentation). Blocks 802-808 represent example instructions for obtaining and analyzing baseline data to create score values. At block 802, the monitoring station 108 obtains baseline GSR data, such as the GSR data 202 illustrated in FIG. 2. The baseline GSR data is obtained while the subject 102 is exposed to a test or sample presentation (e.g., via the presentation device 106). At block 804, the T2P identifier 116 identifies the T2P instances in the baseline GSR data. The T2P value determiner 118 determines the values of the GSR levels of the T2P instances at block 806. At block 808, the score value determiner 119 divides the T2P values into percentiles and assigns score values to the percentiles. In some examples, the percentiles and the score values are stored in the database 114. In some examples, the percentiles represent ranges of GSR levels. The score value determiner 119 may divide the T2P values into any arrangement. For example, as illustrated in the histogram 300 of FIG. 3, score value determiner 119 divides the T2P instances into quartiles, each representing a range of GSR values. In other examples, the score values may be specified for a user or determined in another manner. In such an instance, blocks 802-808 may not be performed. Instead, the example instructions 800 may begin executing at block 810.

At block 810, the monitoring station 108 obtains GSR data (e.g., the GSR data 402) from the subject 102 while the subject 102 is exposed to a target or desired presentation. The presentation may be presented by any presentation device, such as a TV, a speaker, etc. At block 812, the T2P identifier 116 identifies the T2P instances in the GSR data. In some examples, the obtaining of the GSR data (block 810) and the identifying of the T2P instances (block 812) may be performed by one entity, and one or more of the subsequent analyzing processes may be performed by another (separate) entity. In some examples, a first entity may gather the GSR data (block 810) and identify the T2P instances (bock 812) (including the troughs and peaks) and a second entity may analyze the information and generate the GSR intensity profile.

At block 814, the T2P value determiner 118 determines or measures the values or levels of rise in the respective T2P instances. At block 816, the T2P scorer 120 assigns scores (e.g., trough-to-peak scores) to each of the T2P instances. In some examples, the T2P scorer 120 assigns the scores to the troughs of the respective T2P instances. In some examples, the scores are determined based on the score values from the baseline test. For example, as illustrated in FIG. 4, the first T2P instance 404 has a GSR value or level of 0.05 which corresponds to Quartile 1 of the score values. As such, the first T2P instance 404 is assigned a score of 1. In some examples, the scores of the respective T2P instances are assigned or associated with the times of the troughs of the respective T2P instances. For example, as illustrated in FIG. 4, the score of 1 for the first T2P instance 404 is associated with the time at which the trough occurs. In other examples, the scores for the T2P instances may be associated with other parts of the T2P instances (e.g., the peaks, the time of half of the total rise, etc.). In some examples, the scores are plotted or graphed in the score graph 406.

At block 818, the window generator 122 generates or defines a plurality of windows. In some examples, the windows have fixed lengths and are based on a sliding scale. In other words, each of the time windows commences a first time period after a preceding time window and each of the time windows having a duration of a second time period, where the second time period greater than the first time period. Equation 1 above illustrates an example equation for defining a plurality of windows having a fixed length based on a sliding scale. For example, as illustrated in FIG. 5, the first window 502a occurs or spans from T=0 s to T=7 s, the second window 502b occurs from T=1 s to T=8 s, the third window 502c occurs from T=2 s to T=9 s, and so forth. In other words, every increment ($T_S$) a window is defined having a time length ($T_L$). In the illustrated example of FIG. 5, each of the windows 502a-502n has the same length ($T_L$) (e.g., 7 s) using a sliding scale or increment ($T_S$) (e.g., 1 s).

At block 820, the window scorer 124 assigns scores (e.g., window scores) to the windows based on the scores of the T2P instance(s) within the respective windows. For example, as illustrated in the score graph 406 in FIG. 5, the first window 502a includes the score of 1 corresponding to the first T2P instance 404. As such, the window scorer 124 assigns a score of 1 to the first window 502a. This process continues for each of the windows. In some examples, multiple scores for multiple T2P instances are included in a single window. In some examples, the highest score of all of the T2P instances in the window is assigned to the respective window. In some examples, the window scorer 124 assigns the scores to the start times of the respective windows.

Execution of example instructions 800 continues in FIG. 8B. At block 822, the intensity profile generator 126 generates or creates an intensity profile for the presentation based on the scores of the windows. For example, as illustrated in FIG. 5, the intensity profile 500 is generated based on the scores of the windows. In the illustrated example, the scores of the windows are assigned or associated with the times of the beginnings of the respective windows. In other examples, the scores for the windows may be assigned to other points in time occurring (or not occurring) within the respective windows.

In some examples, the GSR intensity profile is normalized or scaled (e.g., from 0-1) at block 824. For example, FIG. 6 illustrates the example graph 602 for the normalized GSR intensity profile 600 of the subject 102 to the presentation. In some examples, the normalized or scaled GSR intensity profile for a subject is averaged with other normalized GSR intensity profiles from one or more other subjects at block 826 to generate the aggregated GSR intensity profile 700. In other examples, the GSR intensity profiles of multiple subjects are averaged first, and then the averaged or aggregated GSR intensity profile is normalized.

The GSR intensity profile 500 for a subject (FIG. 5), the normalized GSR intensity profile 600 for a subject (FIG. 6), and/or the aggregated GSR intensity profile 700 (FIG. 7) may be used to identify elements (e.g., scenes, events, etc.) of the presentation that cause the highest and lowest levels of GSR intensity. The GSR intensity profile 500, as illustrated in the normalized example of FIG. 6, more clearly identifies the areas of the presentation that elicit the strongest responses, as compared to the raw GSR data 402. The GSR intensity profile 500 (FIG. 5), the normalized GSR intensity profile 600 (FIG. 6), and/or the aggregated GSR intensity profile 700 (FIG. 7) may be displayed (e.g., via the monitor 110) and/or generated into a report that is output by the system 100.

In some examples, the GSR intensity profile 500 of one or more subjects (or the aggregated GSR intensity profile 700 (block 826)) may be combined with one or more biometric response measurements to produce an engagement profile (block 828). Additional biometric response measurements may include, for example, heart rate, brain wave data, respiratory response data, body movement data, eye tracking data, facial expression data (e.g., facial emotion encoding), etc. For example, the monitoring station 108 may combine the aggregated GSR intensity profile 700 with data obtained from an eye tracking sensor (e.g., the measurement device(s) 132 of FIG. 1) to determine where the subject 102 is gazing or focused during the presentation when the subject 102 is aroused (e.g., based on the GSR intensity profile). In some examples, the monitoring station 108 may generate a report including the GSR intensity profile 500 (e.g., for a subject), the normalized GSR intensity profile 600 (e.g., for the subject), the aggregated GSR intensity profile 700 and/or the engagement profile (block 830). The aggregated GSR intensity profile 700 and/or the engagement profile may be used to determine the success of one or more portions (e.g., scenes, events, etc.) of the presentation and/or the overall presentation, to determine the effectiveness of one or more portions of the presentation and/or the overall presentation, etc. In some examples, the aggregated GSR intensity profile 700 and/or engagement profile may be used to determine which elements of the presentation elicited or caused high intensity and/or engagement and/or low intensity and/or engagement and, thus, may be modified to increase or decrease the engagement based on the desired outcome. In some examples, the engagement profile is displayed on the monitor 110. Additionally or alternatively, the engagement profile may be printed and distributed, for example. Also, in some examples, the aggregated GSR intensity profile 700 and/or the engagement profile may be used to better predict audience responses to another presentation (e.g., a second or subsequent presentation).

In some examples, the monitoring station 108 identifies one or more elements (e.g., a scene, an event, etc.) in the presentation corresponding to high and/or low intensity and/or engagement based on the aggregated GSR intensity profile 700 and/or the engagement profile (block 832). In some examples, at block 834, the example instructions 800 determine whether one or more elements of the presentation are to be altered or modified based on the identification of the high and/or low intensity and/or engagement element(s). If not, execution of the example instructions 800 may end (block 836). However, if it is determined that one or more elements of the presentation are to be altered or modified (block 834), execution of the example instructions 800 continues and modifies or alters the one or more element(s) (block 838). For example, the effectiveness determiner 128 and/or the presentation modifier 130 may identify an element of the presentation corresponding to a low level of GSR intensity and the presentation modifier 130 may remove or replace the element with another element (e.g., an alternate ending, event, etc.).

After modification of the element(s) (block 838), the example instructions 800 determine whether or not subsequent monitoring of the subject's response is to continue (block 840). If not, execution of the example instructions 800 may end (block 836). However, if monitoring of a subject's response is to continue (block 840), the control returns to block 810 (FIG. 8A) where obtains GSR data is obtained from the subject during the subsequent or continued monitoring, and execution of the example instructions 800 continues as disclosed above.

Figure 9:
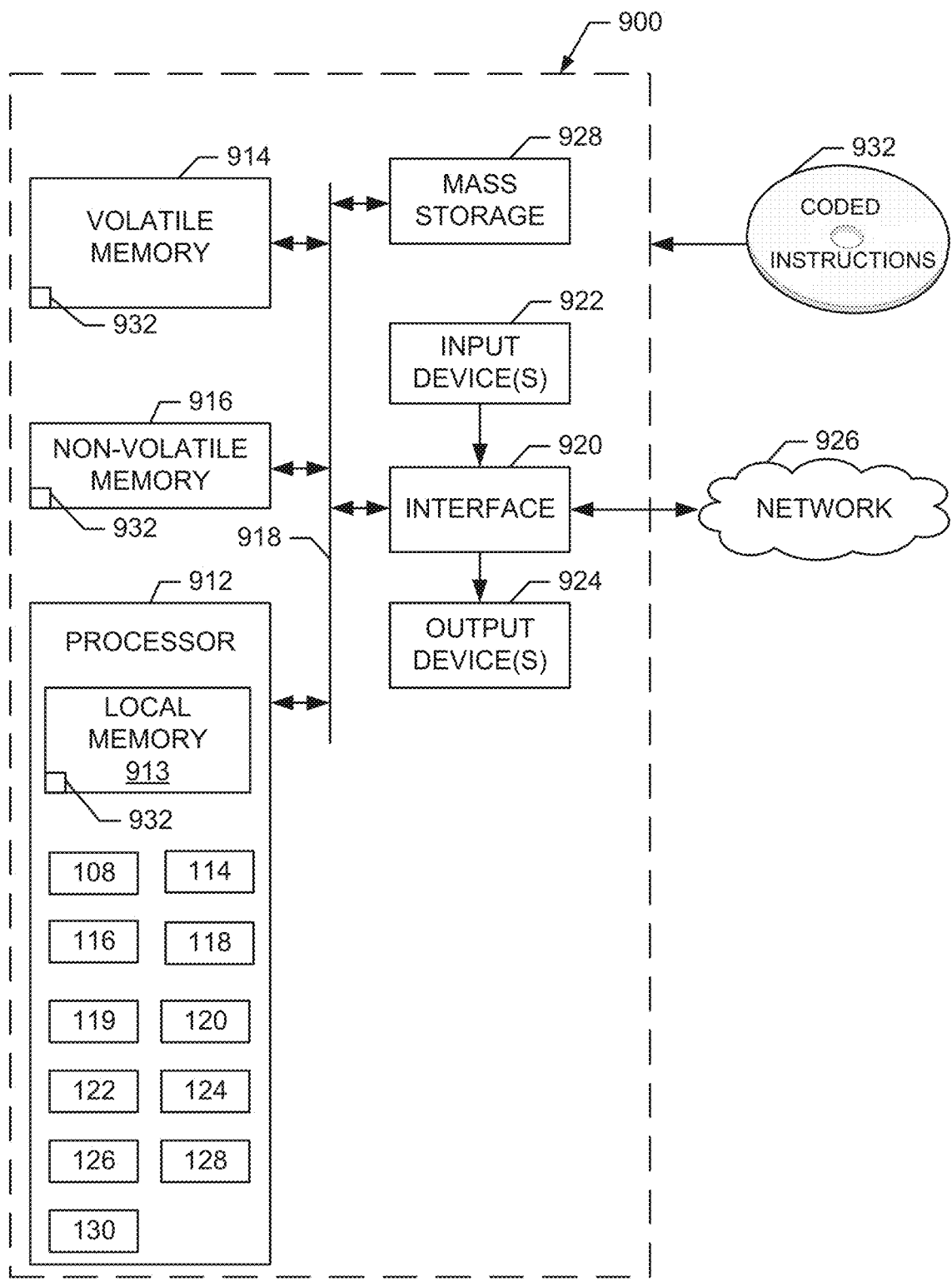
FIG. 9 is a block diagram of an example processor system structured to execute example machine readable instructions represented by FIGS. 8A and 8B to implement the example intensity measurement system of FIG. 1.

FIG. 9 is a block diagram of an example processor platform 900 structured to execute the instructions of FIGS. 8A and 8B to implement the example monitoring station 108, the example database 114, the example T2P identifier 116, the example T2P value determiner 118, the example score value determiner 119, the example T2P scorer 120, the example window generator 122, the example window scorer 124, the example intensity profile generator 126, the example effectiveness determine 128 and/or the example presentation modifier 130 of FIG. 1. By way of example, FIG. 9 shows the example monitoring station 108, the example database 114, the example T2P identifier 116, the example T2P value determiner 118, the example score value determiner 119, the example T2P scorer 120, the example window generator 122, the example window scorer 124, the example intensity profile generator 126, the example effectiveness determine 128 and the example presentation modifier 130, but the processor platform 900 may include more of, fewer of, or different ones of the example monitoring station 108, the example database 114, the example T2P identifier 116, the example T2P value determiner 118, the example score value determine 119, the example T2P scorer 120, the example window generator 122, the example window scorer 124, the example intensity profile generator 126, the example effectiveness determiner 128 and/or the example presentation modifier 130 of FIG. 1. The processor platform 900 can be, for example, a server, a personal computer, a mobile device (e.g., a cell phone, a smart phone, a tablet such as an iPad™), a personal digital assistant (PDA), an Internet appliance, a DVD player, a CD player, a digital video recorder, a Blu-ray player, a gaming console, a personal video recorder, a set top box, or any other type of computing device.

The processor platform 900 of the illustrated example includes a processor 912. The processor 912 of the illustrated example is hardware. For example, the processor 912 can be implemented by one or more integrated circuits, logic circuits, microprocessors or controllers from any desired family or manufacturer.

The processor 912 of the illustrated example includes a local memory 913 (e.g., a cache). The processor 912 of the illustrated example is in communication with a main memory including a volatile memory 914 and a non-volatile memory 916 via a bus 918. The volatile memory 914 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 916 may be implemented by flash memory and/or any other desired type of memory device. Access to the main memory 914, 916 is controlled by a memory controller.

The processor platform 900 of the illustrated example also includes an interface circuit 920. The interface circuit 920 may be implemented by any type of interface standard, such as an Ethernet interface, a universal serial bus (USB), and/or a PCI express interface.

In the illustrated example, one or more input devices 922 are connected to the interface circuit 920. The input device(s) 922 permit(s) a user to enter data and commands into the processor 912. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 924 are also connected to the interface circuit 920 of the illustrated example. The output devices 924 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 920 of the illustrated example, thus, typically includes a graphics driver card, a graphics driver chip or a graphics driver processor.

The interface circuit 920 of the illustrated example also includes a communication device such as a transmitter, a receiver, a transceiver, a modem and/or network interface card to facilitate exchange of data with external machines (e.g., computing devices of any kind) via a network 926 (e.g., an Ethernet connection, a digital subscriber line (DSL), a telephone line, coaxial cable, a cellular telephone system, etc.).

The processor platform 900 of the illustrated example also includes one or more mass storage devices 928 for storing software and/or data. Examples of such mass storage devices 928 include floppy disk drives, hard drive disks, compact disk drives, Blu-ray disk drives, RAID systems, and digital versatile disk (DVD) drives.

The coded instructions 932 of FIGS. 8A and 8B may be stored in the mass storage device 928, in the volatile memory 914, in the non-volatile memory 916, and/or on a removable tangible computer readable storage medium such as a CD or DVD.

From the foregoing, it will be appreciated that methods, apparatus/systems and articles of manufacture have been disclosed that determine an accurate intensity measurement of a subject's biological response, such as GSR, to a presentation. The intensity measurements may be used to identify elements (e.g., scenes, events, etc.) in the presentation that correspond to high and/or low levels of response from the subject. The intensity measurements may therefore be used to better predict how a similar presentation may affect an audience, for example.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A computing system comprising:
   a processor; and
   a non-transitory computer-readable storage medium, having stored thereon program instructions that, upon execution by the processor, cause performance of a set of operations comprising:
   receiving, from a sensor, galvanic skin response (GSR) data for a subject, wherein the GSR data is collected during exposure of the subject to media content during a period of time;
   identifying trough-to-peak instances in the galvanic skin response (GSR) data;
   assigning trough-to-peak values to corresponding ones of the trough-to-peak instances;
   dividing the trough-to-peak values into a plurality of percentiles, wherein each percentile of the plurality of percentiles represents a range of trough-to-peak values;
   assigning a percentile score to each percentile of the plurality of percentiles;
   defining a plurality of windows in the period of time, wherein the plurality of windows comprises at least a first window and a second window, each extending for a fixed time length over the period of time;
   wherein the first window is defined by a first time length in a first subset of the period of time;
   wherein the second window is defined by a second time length in a second subset of the period of time that is different from the first subset; and
   wherein the second subset of the period of time overlaps a portion of the first subset of the period of time;
   assigning window scores to corresponding ones of the windows based on a percentile score of a highest trough-to-peak value occurring within the corresponding ones of the windows to generate a GSR intensity profile;
   comparing the GSR intensity profile to an intensity threshold;
   identifying, based on a comparison of the GSR intensity profile to the intensity threshold, an element of the media content; and
   replacing the element of the media content to satisfy the intensity threshold.

2. The computing system of claim 1, wherein the element of the media content is replaced with a second element based on the second element having a GSR intensity profile that satisfies the intensity threshold during presentation of the second element.

3. The computing system of claim 1, wherein the GSR intensity profile is a first GSR intensity profile; wherein the subject is a first subject exposed to the media content; and wherein the set of operations further comprises:
   averaging the first GSR intensity profile with a second GSR intensity profile for a second subject exposed to the media content to generate an aggregated GSR intensity profile;
   normalizing the aggregated GSR intensity profile to generate a normalized aggregated GSR intensity profile; and
   identifying the element of the media content based on the normalized aggregated GSR intensity profile.

4. The computing system of claim 3, wherein the set of operations further comprises:
  determining an effectiveness of the media content based on the normalized aggregated GSR profile; and
  outputting, to a display, a report based on the normalized aggregated GSR profile.

5. The computing system of claim 3, wherein the set of operations further comprises:
  generating the aggregated GSR profile by averaging a first score occurring at a first time of the first GSR intensity profile with a first score occurring at the corresponding first time of the second GSR intensity profile.

6. The computing system of claim 1, wherein the GSR intensity profile is a first GSR intensity profile; wherein the subject is a first subject exposed to the media content; and wherein the set of operations further comprises:
  normalizing the first GSR intensity profile to generate a normalized first GSR intensity profile;
  averaging the normalized first GSR intensity profile with a second normalized GSR intensity profile for a second subject exposed to the media content to generate a normalized aggregated GSR intensity profile; and
  identifying the element of the media content based on the normalized aggregated GSR intensity profile.

7. The computing system of claim 1, wherein the set of operations further comprises:
  assigning the percentile score of the highest trough-to-peak value occurring during the first window of the plurality of windows to a start time of the first window.

8. The computing system of claim 1, wherein the element of the media content corresponds to at least a scene in the media content.

9. The computing system of claim 2, wherein the GSR intensity profile is a first GSR intensity profile; wherein the subject is a first subject exposed to the media content; and wherein the set of operations further comprises:
  generating a second GSR intensity profile for the first subject based on second GSR data collected from the first subject during exposure of the first subject to the media content including the second element.

10. The computing system of claim 6, the set of operations further comprising:
  determining a number of times that the window scores of the aggregated GSR intensity profile satisfies the intensity threshold over the period of time by comparing the window scores of the aggregated GSR intensity profile to the intensity threshold.

11. A non-transitory machine-readable storage medium having stored thereon program instructions that, upon execution by a processor, cause performance of a set of operations comprising:
  receiving, from a sensor, galvanic skin response (GSR) data for a subject, wherein the GSR data is collected during exposure of the subject to media content during a period of time;
  identifying trough-to-peak instances in the GSR data for the subject, the GSR data collected from the subject during exposure of the subject to media content during a period of time;
  assigning trough-to-peak values to corresponding ones of the trough-to-peak instances;
  dividing the trough-to-peak values into a plurality of percentiles, wherein each percentile of the plurality of percentiles represents a range of trough-to-peak values;
  assigning a percentile score to each percentile of the plurality of percentiles;
  defining a plurality of windows in the period of time,
    wherein the plurality of windows comprises at least a first window and a second window, each extending for a fixed time length over the period of time;
    wherein the first window is defined by a first time length in a first subset of the period of time;
    wherein the second window is defined by a second time length in a second subset of the period of time that is different from the first subset; and
    wherein the second subset of the period of time overlaps a portion of the first subset of the period of time;
  assigning window scores to corresponding ones of the windows based on a percentile score of a highest trough-to-peak value occurring within the corresponding ones of the windows to generate a GSR intensity profile;
  comparing the GSR intensity profile to an intensity threshold;
  identifying, based on a comparison of the GSR intensity profile to the intensity threshold, an element of the media content; and
  replacing the element of the media content to satisfy the intensity threshold.

12. A method comprising:
  receiving, from a sensor, galvanic skin response (GSR) data for a subject, wherein the GSR data is collected during exposure of the subject to media content during a period of time;
  identifying, by execution of an instruction with a processor, trough-to-peak instances in the GSR data for the subject, the GSR data collected from the subject during exposure of the subject to media content during a period of time;
  assigning, by execution of an instruction with the processor, trough-to-peak values to corresponding ones of the trough-to-peak instances;
  dividing the trough-to-peak values into a plurality of percentiles, wherein each percentile of the plurality of percentiles represents a range of trough-to-peak values;
  assigning a percentile score to each percentile of the plurality of percentiles;
  generating, by execution of an instruction with the processor, at least two windows in the period of time,
    wherein the at least two windows comprises at least a first window and a second window, each extending for a fixed time length over the period of time;
    wherein the first window is defined by a first time length in a first subset of the period of time;
    wherein the second window is defined by a second time length in a second subset of the period of time that is different from the first subset; and
    wherein the second subset of the period of time overlaps a portion of the first subset of the period of time;
  generating, by execution of an instruction with the processor, at least one GSR intensity profile by assigning window scores to corresponding windows of the at least two windows based on a percentile score of a highest trough-to-peak value occurring within the corresponding ones of the windows;
  comparing, by execution of an instruction with the processor, the at least one GSR intensity profile to an intensity threshold;
  identifying, by execution of an instruction with the processor and based on a comparison of the at least one GSR intensity profile to the intensity threshold, an element of the media content;

and
replacing, by execution of an instruction with a processor, the element of the media content to satisfy the intensity threshold.

13. The method of claim 12, wherein the element of the media content is replaced with a second element based on the second element having a GSR intensity profile that satisfies the intensity threshold during presentation of the second element.

14. The method of claim 12, wherein the GSR intensity profile is a first GSR intensity profile; wherein the subject is a first subject exposed to the media content; and wherein generating the at least one GSR intensity profile comprises:
   averaging a first GSR intensity profile with a second GSR intensity profile for a second subject exposed to the media content to generate an aggregated GSR intensity profile;
   normalizing the aggregated GSR intensity profile to generate a normalized aggregated GSR intensity profile; and
   identifying the element of the media content based on the normalized aggregated GSR intensity profile.

15. The method of claim 14, further comprising:
   determining effectiveness to determine an effectiveness of the media content based on the normalized aggregated GSR profile; and
   outputting, to a display, a report based on the normalized aggregated GSR profile.

16. The method of claim 14, further comprising:
   associating, by execution of an instruction with the processor, the respective ones of the trough-to-peak values with a time corresponding to a trough of each trough-to-peak instance.

17. The method of claim 12, wherein the GSR intensity profile is a first GSR intensity profile; wherein the subject is a first subject exposed to the media content; and wherein generating the at least one GSR intensity profile comprises:
   normalizing a first GSR intensity profile to generate a normalized first GSR intensity profile;
   averaging the normalized first GSR intensity profile with a second normalized GSR intensity profile for a second subject exposed to the media content to generate a normalized aggregated GSR intensity profile; and
   identifying the element of the media content based on the normalized aggregated GSR intensity profile.

18. The method of claim 12, wherein generating the at least one GSR intensity profile assigns the percentile score of the highest trough-to-peak value occurring during the first window of the at least two windows to a start time of the first window.

19. The method of claim 13, wherein the GSR intensity profile is a first GSR intensity profile; wherein the subject is a first subject exposed to the media content; and wherein generating the at least one GSR intensity profile comprises:
   generating a second GSR intensity profile for the first subject based on second GSR data collected from the first subject during exposure of the first subject to the media content including the second element.

20. The method of claim 14, further comprising:
   determining a number of times that the window scores of the aggregated GSR intensity profile satisfies the intensity threshold over the period of time by comparing the window scores of the aggregated GSR intensity profile to the intensity threshold.

\* \* \* \* \*